Reissued Dec. 4, 1928.

Re. 17,153

UNITED STATES PATENT OFFICE.

MAUDE AGNES MINGUS, FORMERLY MAUDE AGNES MINGUS WHEELER, OF OAKLAND, CALIFORNIA.

HAIR DYE.

No Drawing. Original No. 1,638,341, dated July 19, 1927, Serial No. 759,100, filed December 31, 1924. Application for reissue filed September 11, 1928. Serial No. 305,310.

My invention is a hair rinse preparation, preferably sold in the form of powder and used as a tinting color, or as sometimes designated in the trade, a glint. My hair rinse comprises an acid and a dye, of a slight tint, mixed and powdered which when dissolved in water form a rinse water. I may use dyes which with the acid will dissolve in water or dyes held in suspension. My specific preparation comprises tartaric acid with a coal-tar or vegetable dye mixed in suitable proportions, and generally sold in the form of powder, to be dissolved by the user when wanted.

My rinse powders are preferably used after the hair has been shampooed, thoroughly washed and rinsed in clear water, then the rinse tint is applied to the hair by immersing the hair in the rinse or dipping it over the hair until all or nearly all of the color has been taken out of the water. This is a final application to the hair and it is not supposed to be rinsed, but if it is found that the hair has absorbed too much of the color it may be partly washed out with a clear water rinse. After treatment the hair should be well dried and brushed to bring out the luster. My invention is not to be confused with hair dyes which give a permanent color to the hair, whether sold in powder or liquid form.

The preferred proportions are ten pounds of commercial tartaric acid crystals or powder mixed with three teaspoonsful of the dye and made into a powder. I may use vegetable dyes such as henna, sufficient to give a slightly reddish tinge, or the coal tar equivalent thereof. I may use various colors or mixture of colors to secure the desired effect. The color should be chosen to harmonize with the hair and heighten or increase its natural tint. Thus for dark brown hair a dark dye would be used, a slightly reddish dye much fainter than henna may be used to give a golden brown effect.

It will be understood that the proportions may be changed, both of tartaric acid and of the dye to give the desired effect. The rinse powders are preferably sold in packages with directions for dissolving in water, which manifestly may be varied in quantity as also the strength may be varied by using two or more powders.

The rinse is used, as before described, as a final application after the hair has been shampooed and rinsed, to give a faint tint or glint to the hair. The action of the tartaric acid is to soften the water, but it has a more important function in that it partially fixes the dye in the hair. In the latter respect, its action is not pronounced, but does result in the retention of the glint longer than it would be retained if the acid were not used.

I claim:—

1. A hair rinse powder comprising tartaric acid and a coal tar dye.

2. A hair rinse powder comprising a crystalline mild organic acid, and a coal tar dye.

3. A hair rinse powder comprising substantially ten pounds of tartaric acid and three teaspoonsful of a coal tar dye.

4. A hair rinse powder comprising substantially ten pounds of a crystalline mild organic acid, and a coal tar dye.

Signed at the city and county of San Francisco, State of California, this 31st day of August, 1928.

MAUDE AGNES MINGUS.